US012544256B2

(12) United States Patent
Deckman et al.

(10) Patent No.: US 12,544,256 B2
(45) Date of Patent: Feb. 10, 2026

(54) IUD REMOVAL DEVICES, AND RELATED METHODS AND KITS

(71) Applicant: MEDICINES360, San Francisco, CA (US)

(72) Inventors: Rob Deckman, San Bruno, CA (US); Chinmay Deodhar, Hanover (DE); Dominic Peralta, San Mateo, CA (US); Mitchell David Creinin, Davis, CA (US)

(73) Assignee: MEDICINES360, San Francisco, CA (US)

( * ) Notice: Subject to any disclaimer, the term of this patent is extended or adjusted under 35 U.S.C. 154(b) by 233 days.

(21) Appl. No.: 18/464,226

(22) Filed: Sep. 10, 2023

(65) Prior Publication Data

US 2024/0091052 A1 Mar. 21, 2024

Related U.S. Application Data

(60) Provisional application No. 63/375,879, filed on Sep. 16, 2022.

(51) Int. Cl.
*A61F 6/18* (2006.01)
*A61F 6/14* (2006.01)

(52) U.S. Cl.
CPC ................ *A61F 6/18* (2013.01); *A61F 6/144* (2013.01)

(58) Field of Classification Search
CPC .. A61F 6/144; A61F 6/18; A61F 6/225; A61F 6/22; A61F 6/142; A61F 6/14; A61F 6/12; A61F 6/06; A62B 18/08; A62B 18/02; A41D 13/1192; A41D 31/30; A61L 2/183; A61L 2/186; A61L 2101/02; A61L 2202/11; A61L 2202/26; A61L 2420/02; A61L 2420/08; A61L 2/022; A61K 9/0036; A61K 9/0039
See application file for complete search history.

(56) References Cited

U.S. PATENT DOCUMENTS 2,442,066 A 5/1948 Waterbury
2,534,900 A 12/1950 Chalmers
(Continued)

FOREIGN PATENT DOCUMENTS

CN 2805723 8/2006
CN 209464167 U 10/2019
(Continued)

*Primary Examiner* — Ophelia A Hawthorne
(74) *Attorney, Agent, or Firm* — Fishman Stewart PLLC; Cecily Anne O'Regan

(57) ABSTRACT

A self-removal device for intrauterine device (IUD) extraction is described that includes a housing having a proximal handle and a distal aperture, and a grasper mechanism with stationary and movable elements for engaging and securing IUD threads, wherein the grasper is actuated by a lever positioned at the housing. Systems are also described comprising the device and ancillary components such as locking elements, grips, linkage assemblies, as well as kit embodiments that may include visualization aids, light sources, forceps, measuring tools, and instructions for use. A patient using the device, with or without assistance, can independently or semi-independently remove an IUD using the device and system in non-clinical settings, optionally with remote digital guidance or confirmation.

24 Claims, 10 Drawing Sheets

(56) References Cited

U.S. PATENT DOCUMENTS

| | | | |
|---|---|---|---|
| 3,407,806 | A | 10/1968 | Hulka et al. |
| 3,635,215 | A | 1/1972 | Shea et al. |
| 3,783,861 | A | 1/1974 | Abramson |
| 3,794,025 | A | 2/1974 | Lerner |
| 3,902,483 | A | 9/1975 | Place et al. |
| 3,937,217 | A | 2/1976 | Kosonen |
| 4,022,198 | A | 5/1977 | Johnson |
| 4,353,363 | A | 10/1982 | Quesada |
| 4,359,046 | A | 11/1982 | Shaw, Jr. |
| 4,372,302 | A | 2/1983 | Akerlund |
| 4,381,001 | A | 4/1983 | Shaw, Jr. |
| 4,495,934 | A | 1/1985 | Shaw, Jr. |
| 4,561,433 | A | 12/1985 | Wheeler et al. |
| 4,830,025 | A | 5/1989 | Gainutdinova et al. |
| 4,920,727 | A | 5/1990 | Ristimaki et al. |
| 4,949,732 | A | 8/1990 | Spoon et al. |
| 4,957,119 | A | 9/1990 | Nijs |
| 5,084,004 | A | 1/1992 | Ranoux |
| 5,088,505 | A | 2/1992 | Nijs |
| 5,370,129 | A | 12/1994 | Diaz et al. |
| 5,400,804 | A | 3/1995 | Helle et al. |
| 5,785,053 | A | 7/1998 | Macandrew et al. |
| 6,039,968 | A | 3/2000 | Nabahi |
| 6,056,976 | A | 5/2000 | Markkula et al. |
| 6,063,395 | A | 5/2000 | Markkula et al. |
| 6,103,256 | A | 8/2000 | Nabahi |
| 6,117,442 | A | 9/2000 | Markkula et al. |
| 6,599,296 | B1 | 7/2003 | Gillick et al. |
| 7,862,552 | B2 | 1/2011 | McIntyre et al. |
| 8,690,892 | B2 | 4/2014 | Rizvi |
| 10,028,858 | B2 | 7/2018 | Deckman et al. |
| 2005/0045183 | A1 | 3/2005 | Callister et al. |
| 2008/0077097 | A1 | 3/2008 | Chambers et al. |
| 2008/0095825 | A1 | 4/2008 | Lafont |
| 2016/0038018 | A1 | 2/2016 | Wilson et al. |
| 2016/0217707 | A1 | 7/2016 | Jutila et al. |
| 2018/0303499 | A1 | 10/2018 | Bonneau et al. |
| 2020/0031544 | A1 | 1/2020 | Choi |
| 2020/0261258 | A1 * | 8/2020 | Deckman ................ A61F 6/144 |

FOREIGN PATENT DOCUMENTS

| | | | |
|---|---|---|---|
| CN | 211023425 | | 7/2020 |
| DE | 3222795 | A1 | 12/1983 |
| WO | 2005112806 | A2 | 12/2005 |
| WO | 2017173178 | A1 | 10/2017 |
| WO | 2018069285 | A1 | 4/2018 |
| WO | 2020172246 | A2 | 8/2020 |
| WO | 2024059484 | A1 | 3/2024 |

* cited by examiner

IUD REMOVAL DEVICES, AND RELATED METHODS AND KITS

CROSS-REFERENCE

This application claims the benefit of U.S. Provisional Application No. 63/375,879, filed Sep. 16, 2022, entitled IUD REMOVAL DEVICES, AND RELATED METHODS AND KITS which application is incorporated herein in its entirety by reference.

BACKGROUND

Field

The disclosure relates generally to devices for removing an intrauterine device (IUD).

Background

The rates of unwanted pregnancies in developing and developed countries have continued to decrease over the last 10 years. However, barriers to accessing contraception is still a significant issue for jurisdictions where access to healthcare is limited. According to the World Health Organization (WHO) additional barriers to access contraception can be based on age, marital status, health worker bias, and/or lack of willingness to acknowledge sexual health needs. Knowledge, transportation and financial constraints are also significant barriers to access.

Improving access to contraception continues to be an important objective for a variety of reasons. Adolescent pregnancy remains a major contributor to maternal and child mortality and to intergenerational cycles of ill-health and poverty. Although there are several types of contraception available, the intrauterine device (IUD) continues to be a reliable, easy to deploy, low cost option for preventing unplanned pregnancies. However, accessibility to the IUD as a contraceptive method for women living in underserved communities continues to be a challenge due to lack of access to a medical clinic or physician.

What is needed are methods, devices, systems and kits that can be used for IUD removal by a patient or a patient and a partner in a remote location when access to a medical clinic or physician is not readily available.

SUMMARY

Disclosed are methods, devices, systems and kits for IUD removal by a patient or a patient and a partner when access to a medical clinic or a physician is not available. Partners can include, for example, local health care promoters, nurse practitioners, friends or relatives.

Both the foregoing general description and the following detailed description are exemplary and explanatory only and are not restrictive of the disclosed embodiments, as claimed.

INCORPORATION BY REFERENCE

All publications, patents, and patent applications mentioned in this specification are herein incorporated by reference to the same extent as if each individual publication, patent, or patent application was specifically and individually indicated to be incorporated by reference.

U.S. Pat. No. 2,442,066 A to Waterbury issued May 25, 1948;

U.S. Pat. No. 3,407,806 A to Hulka et al. issued Oct. 29, 1968;

U.S. Pat. No. 3,635,215 A to Shea et al. issued Jan. 18, 1972;

U.S. Pat. No. 3,902,483 A to Place et al. issued Sep. 2, 1975;

U.S. Pat. No. 3,937,217 A to Kosonen issued Feb. 10, 1976;

U.S. Pat. No. 4,022,198 A to Johnson issued May 10, 1977;

U.S. Pat. No. 4,359,046 A to Shaw Jr. issued Nov. 16, 1982;

U.S. Pat. No. 4,372,302 A to Akerlund issued Feb. 8, 1983;

U.S. Pat. No. 4,381,001 A to Shaw Jr. issued Apr. 26, 1983;

U.S. Pat. No. 4,495,934 A to Shaw Jr. issued Jan. 29, 1985;

U.S. Pat. No. 4,561,433 A to Wheeler et a. issued Dec. 31, 1985;

U.S. Pat. No. 4,830,025 A to Gainutdinova et al. issued May 16, 1989;

U.S. Pat. No. 5,785,053 A to Macandrew et al. issued Jul. 28, 1998;

U.S. Pat. No. 6,599,296 B2 to Gillick et al. issued Jul. 29, 2003

U.S. Pat. No. 10,028,858 B2 to Deckman et al. issued Jul. 24, 2018;

U.S. Patent Pub. US 2016/0038018 A1 to Wilson et al. published Feb. 11, 2016;

U.S. Patent Pub. US 2020/00261258 A1 to Deckman et al. published Aug. 20, 2020;

WO 2017/173178 A1 to Ramanujam et al. published Oct. 5, 2017; and

WO 2018/069285 A1 to Mikkonen et al. published Apr. 19, 2018.

BRIEF DESCRIPTION OF THE DRAWINGS

The novel features of the invention are set forth with particularity in the appended claims. As will be appreciated by those skilled in the art, the various features illustrated in the drawings may not be drawn to scale. Moreover, the illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

A better understanding of the features and advantages of the present invention will be obtained by reference to the following detailed description that sets forth illustrative embodiments, in which the principles of the invention are utilized, and the accompanying drawings of which.

DETAILED DESCRIPTION

Figure 1B:
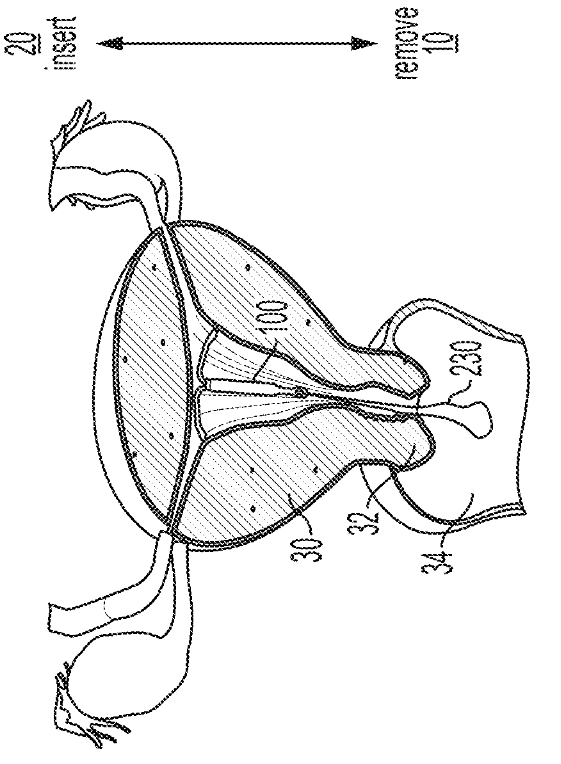
FIG. 1B PRIOR ART
FIG. 1B is a t-shaped IUD positioned within a uterus.

Throughout the disclosure and figures the following markings have been used: a axis; 10 proximal or proximal position; and 20 distal or distal position. The proximal position reflects the location nearest the user's hand in use; the distal position reflects the location furthest from the user's hand in use. The axis is an axis about which an action occurs.

The IUD removal devices disclosed herein are sized to at least partially fit within a female vagina 34 and to allow the device to approach and/or engage the cervix 32. As will be appreciated by those skilled in the art, although there is variability in the actual length and width of the vagina, the female vaginal anatomy can typically be organized into sizes and tools engaging the female vaginal anatomy can also be organized into sizes. The average depth of the vagina (measured from the opening to the tip of the cervix) is about 3.77 inches (9.6 cm), and the size range has been reported to be from about 3 inches to 7 inches (7.6 cm to 17.7 cm). The cervix is typically about 1 inch (about 2 cm to 3 cm) in length.

In general, the removal devices disclosed herein will have a dimension of the longitudinal body (e.g., the portion that is inserted) in a range of from 3.1 inches (80 mm) to 5.1 inches (130 mm) in length, more preferably 3.5 inches (90 mm) to 4.7 inches (120 mm) in length, and even more preferably 4.1 inches (105 mm) to 4.2 inches (108 mm) in length. The overall diameter of the distal end 20 of the devices are from 0.39 inches (10 mm) to 1.25 inches (31.75 mm), more preferably from 0.47 inches (12 mm) to 1.10 (27.9 mm), and even more preferably 1.00 inch (25 mm). The size of the diameter can be selected to facilitate keeping the walls of the vagina out of the way during use. For example, a diameter of 1.00 inch is optimized for insertion with keeping the walls of the vagina out of the way. The handle of the devices can have a larger diameter than the distal (insertion) end of the devices and be oriented either in line with the longitudinal axis (e.g., 0 degree from the longitudinal axis), or at a varying angle from the longitudinal axis up to 90 degrees from the longitudinal axis A.

I. Intrauterine Devices (IUDs)

Figure 1A:
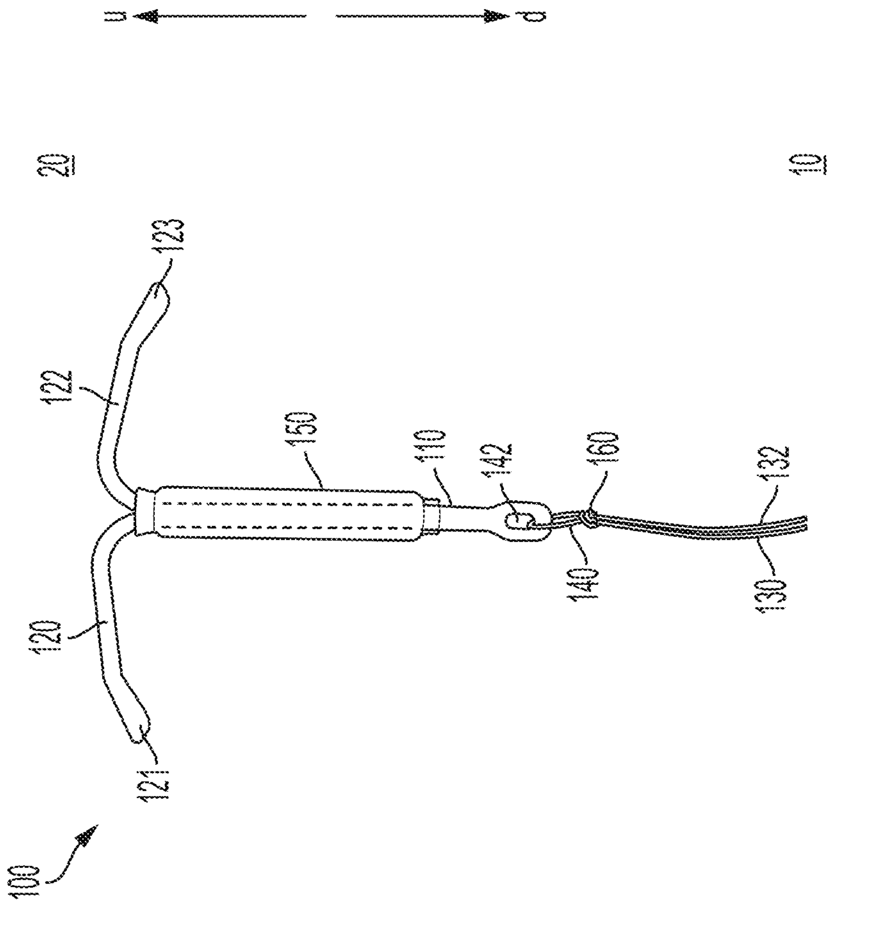
FIG. 1A PRIOR ART
FIG. 1A is a t-shaped IUD.

FIG. 1A is a T-shaped IUD 100. IUDs typically have a length of from about 31.90 mm to about 32.22 mm and a width of from about 31.81 mm to about 32.13 mm when the IUD is in a fully deployed position. As will be appreciated by those skilled in the art, the length does not include the knot or removal threads that may accompany the IUD.

The T-shaped IUD 100 comprises an elongated body 110 having a proximal end 10 and a distal end 20. The elongated body 110 can include a coating such as a time-release drug, hormone, or copper. A drug delivery T-shaped IUD 100 typically has four components: the T-shaped IUD 100, the removal thread at the proximal end of the IUD, a drug reservoir and an exterior membrane surrounding the drug reservoir that enables the drug in the reservoir to be time-released.

The elongated body 110 can be formed from any suitable material, including, but not limited to plastic or copper. At the distal end 20 of the IUD (i.e., the end positioned away from the physician's hand), IUD arms 120, 122 are attached to or integrally formed with the elongated body 110. The IUD arms 120, 122 are configurable to fold upward u or downward d to minimize the IUD cross-section such that the IUD can fit within an interior of an insertion device sheath or tube for insertion through the cervix and into the uterus. Additionally, either or both of the IUD arms 120, 122 are configurable to include an enlarged or bulbous tip 121, 123, which can, for example, have a curved, spherical or semi-spherical shape. The bulbous tip 121, 123 of the IUD arms 120, 122 can be formed such that the IUD arms, when folded upward u and pushed together, form a smooth and rounded distal tip. The IUD is not shipped or stored with the arms folded up to avoid deforming the arms.

At a proximal end 10 of the T-shaped IUD 100, the IUD can further include one or more IUD threads 130, 132 (or strings) attached to the IUD. The IUD threads 130, 132 are connectable to the IUD at a connection point 140, e.g., a single thread with two ends passed through an aperture and tied in a knot as illustrated. The connection point 140 can have an aperture 142 through which the string passes. The IUD thread can also be configured to form a loop through the connection point.

The IUD device can also release a time-released drug, active agent, or hormone. For example, when the T-shaped IUD 100 has an elongate member fabricated of polyethylene equipped with a reservoir adjusted around the elongate member, the reservoir can contain, for example, the hormone levonorgestrel. The reservoir 150 containing the active agent can also be covered with a polymer membrane that controls the release rate of the drug. The active agent can also include, for example, hormones used for the treatment of menopausal troubles or hormones used for contraception. A membrane can be provided which encloses the reservoir 150 and provides for a time-release of the hormone in the reservoir.

As packaged, the T-shaped IUD 100 is positioned at the forward end of the insertion device with the hormone-containing reservoir protected by an outer tube. The IUD arms 120, 122 of the transverse member, on the other hand, are allowed to reside outside the outer tube to prevent creep or shape set of the arms during shipment and storage prior to use. The IUD threads 130, 132 allow the T-shaped IUD 100 to be retracted during removal, are within an interior of the insertion device and extend from a proximal end.

FIG. 1B is an exemplar T-shaped IUD 100 with a looped IUD thread 132 positioned within a uterus 30. Other thread configurations can be used without departing from the scope of the disclosure. As would be understood by those skilled in the art, the uterus 30 is accessed via the cervix 32 which is located within the vagina 34. The T-shaped IUD 100 is similar to the IUD shown in FIG. 1A in that it includes an elongated body 110, IUD arms 120, 122 and a connection point 140. However, in this configuration, the looped IUD thread 134 (or string) is provided which forms a loop at the proximal end 10 (the end positioned within the vagina 34). The use of a looped IUD thread 134 provides a mechanism for allowing the IUD thread to be captured for an easier removal of the T-shaped IUD 100.

In some configurations, the IUD threads 130, 132 or looped IUD thread 134 can have a series of knots 160 or beads (not shown) along its length at intervals to assist in the removal process. The one or more knots 160 can be formed by tying each IUD thread in individual knots along the length of the IUD thread. Where beads are used, a small bead can be attached or incorporated into each IUD thread along the length of the IUD thread. The knots or beads would be positioned along the length of the IUD threads at a location along the length of the IUD thread that would be positioned outside the cervix. For the looped IUD thread 134, knots or beads can be provided along a length of the looped IUD thread 134 that is located outside the cervix 32 and within the vagina 34.

II. Removal Devices and Systems

FIGS. 2-A-G illustrate an IUD removal device 200. The IUD removal device 200 is suitable for self-removal of an IUD or removal of an IUD outside a health clinic setting. The IUD removal device 200 can be part of a system.

The IUD removal devices 200 comprise: a housing 210 defining a cavity having a handle 220 at a proximal end and an aperture at a distal end; a grasper positioned within the cavity wherein the grasper extends outside the aperture at the distal end, the grasper comprising a first stationary grasper element with a first facing surface, and a second moveable grasper element with a second facing surface, wherein the first facing surface is positioned to face the second facing surface; a lever 224 is positioned adjacent the handle 210 wherein the lever 224 is operable to control the grasper when the lever 224 is moved from a first position to a second position; and an actuating link in communication with the lever at a first end and the second moveable grasper element at a second end.

Figure 2A:
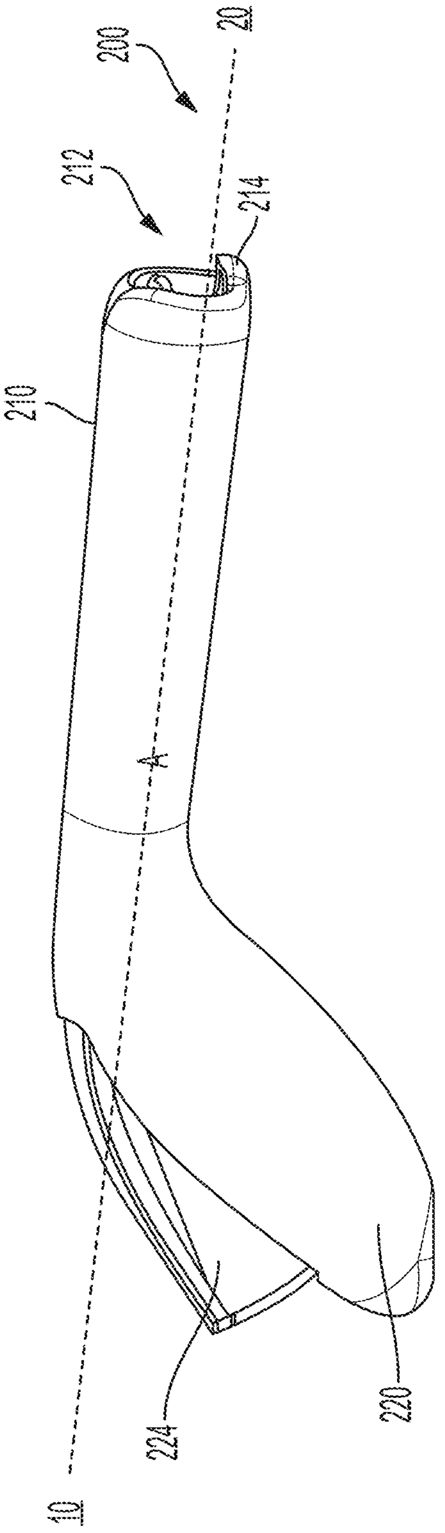
FIGS. 2-A-G illustrate an IUD removal device with the IUD grasper in an open configuration (FIG. 2A), with the grasper in a closed configuration (FIG. 2B), interior views (FIG. 2C-F), and an exploded view of the parts (FIG. 2G)
Figure 2B:
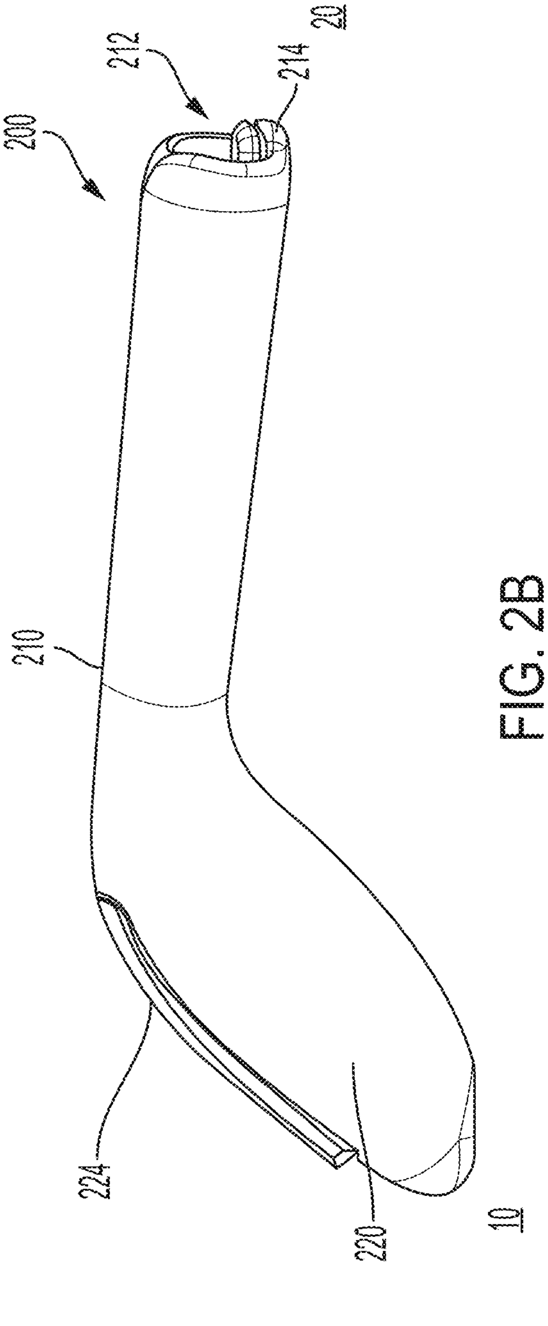
Figure 2C:
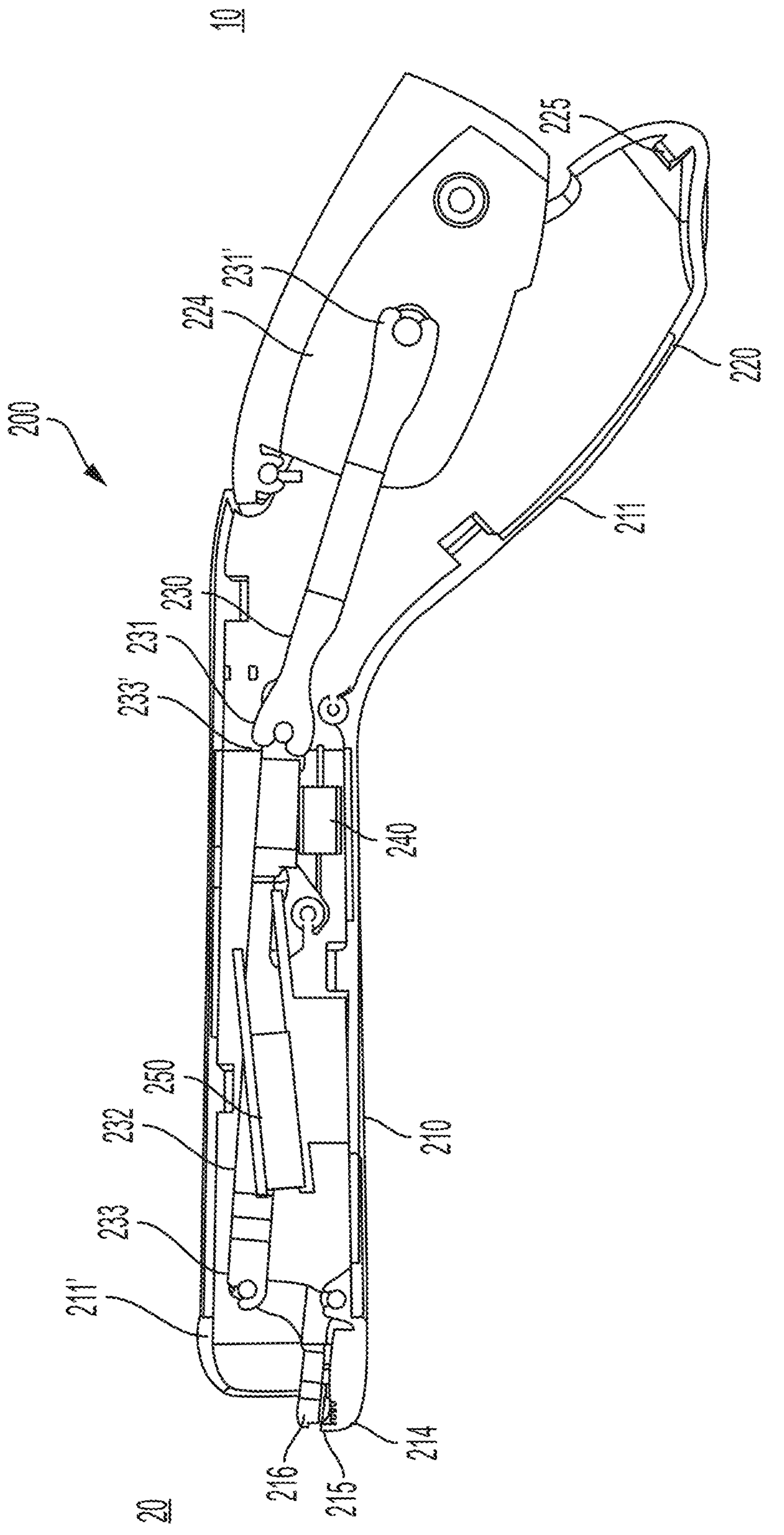
Figure 2D:
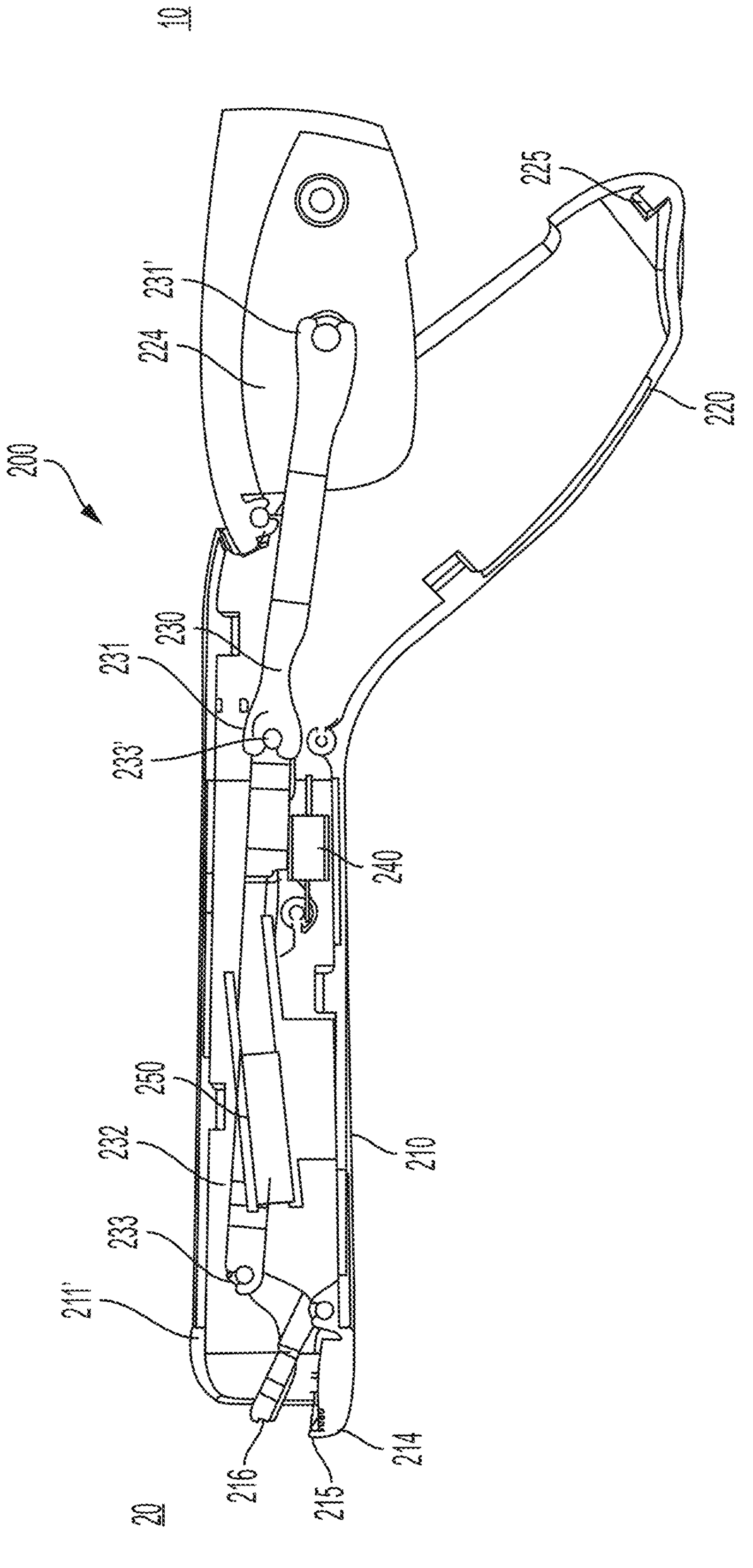
Figure 2E:
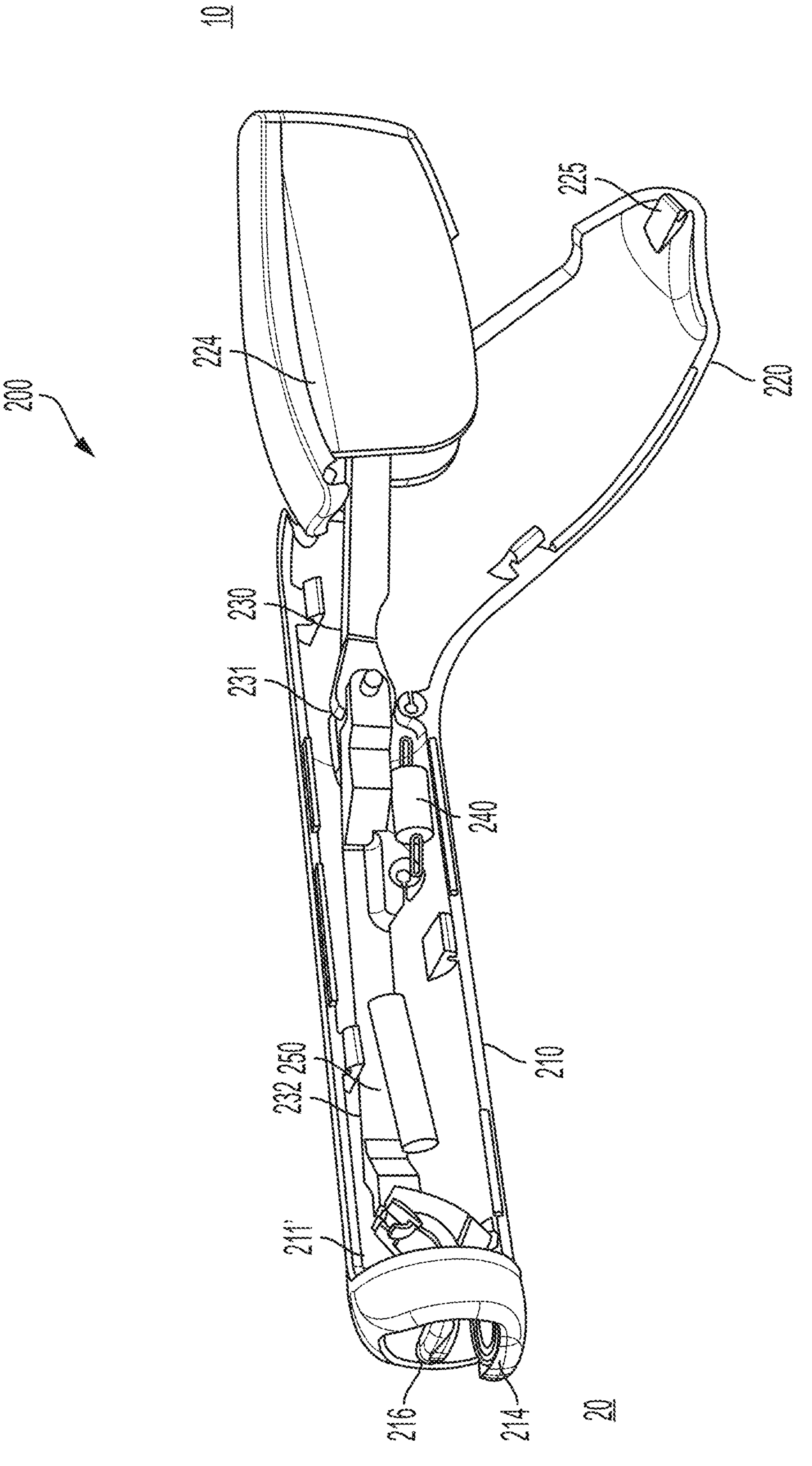

FIGS. 2A, 2D, and 2E illustrate the IUD removal device 200 in an open configuration from an exterior view (FIG. 2A), and interior views (FIGS. 2D and 2E). The IUD removal device 200 has a housing 210 with a handle 220 at the proximal end 10, and an aperture 212 at the distal end 20. The housing defines a cavity therein. The proximal end 10 engages a user's hand and the distal end 20 is positionable within the vagina. A lever 224 is provided that is operable to control movement of the grasper at the distal end 20 when securing the IUD strings of the IUD. The grasper has a first grasper element 214 and a second grasper element 216. Each of the grasper elements have an interiorly facing surface. The interiorly facing surface of the first grasper faces the interiorly facing surface of the second grasper. When the IUD removal device has an IUD string positioned between the first grasper and the second grasper, the interiorly facing surfaces are brought into contact with one another by activating the lever. Depending on whether the interiorly facing surfaces are smooth or have surface treatment the surfaces will either make complete surface to surface contact or will make sufficient surface to surface contact to secure the IUD threads between the facing grasper surfaces.

The grasper can extend fully or partially out of the aperture 212. When activated, the first grasper element 214 and the second grasper element 216 have facing surfaces that mate or come into contact with one another, e.g. are positionable to face one another. The facing surfaces can be two flat surfaces. A raised leading edge 215 can be provided on at least one grasper element to facilitate engaging or grasping the threads of the IUD with the grasper. A gripping surface, such as a textured surface, teeth, and/or ridges, can also be provided on the interior surface of one or both of the grasper elements such that the gripping surface on the interior surface faces the interior surface of the opposing grasper element. The gripping surface can be a surface that is integrally formed with the grasper element or can be a surface treatment applied to the grasper element. The IUD removal devices are operable to be in communication with one or more of a camera, a speaker and a screen. One or more of the camera, speaker and screen can be incorporated into the IUD removal device or can be associated with an external electronic device, such as a mobile phone or tablet. The external electronic device is secondary to the IUD removal device.

As illustrated in FIGS. 2A-F, the first grasper element 214 is not moveable and is formed integrally with the housing of the removal device 200. The second grasper element 216 is moveable to engage the first grasper element 214 in use. As will be appreciated by those skilled in the art, the first grasper element 214 can be formed separate from the IUD removal device 200 and be moveable with movement of the second grasper element 216. The first grasper element 214 can be stationary while the second grasper element 216 is a moveable grasper element.

The lever 224 is shown extended away from the body of the IUD removal device 200 in FIG. 2A when the grasper is open (e.g., when the first grasper element 214 and the second grasper element 216 are spaced apart). The lever 224 is shown adjacent the body of the IUD removal device 200 in FIG. 2B when the grasper is closed (e.g., when the first grasper element 214 and the second grasper element 216 are in contact).

Turning to FIGS. 2C-G, interior views of the IUD removal device 200 (FIGS. 2C-F) and an exploded parts view (FIG. 2G) are illustrated. In FIG. 2C the lever 224 is shown positioned within the handle 220 in the closed position with a substantial portion of the lever 224 body positioned within the interior of the handle 220. The IUD removal device 200 has a body or housing with a right side and a left side and a plurality of coupling surfaces 225 that allows the right side and the left side of the body to be securely engaged when the two sides of the are put together. The coupling surfaces can be a plurality of detent features. The detent features provide a catch between the first portion of the housing and the second portion of the housing to hold the housing components securely together when the device is compiled until such time as it may be desirable to release the detent to allow access to the interior of the housing.

The lever 224 is operable to engage a plurality of links. As illustrated, the lever 224 engages an actuating link 230. The actuating link 230 is an elongated arm with a first actuating link mating surface 231 and a second actuating link mating surface 231' wherein the first actuating link mating surface is positioned at a first end of the actuating link 230 and the second actuating link mating surface is positioned at a second end (opposite end) of the actuating link 230. The actuating link mating surfaces are shown as concave or c-shaped. The first concave surface of the first actuating link mating surface 231 couples with a mating surface on a horizontal link 232. The second concave surface of the second actuating link mating surface 231' couples with a lever mating surface positioned within the body of the lever 224. The mating surface within the lever 224 is shown as a cylindrical shape that extends from the an interior surface of the lever. The second concave surface allows the actuating link 230 to rotate about an axis during use when the lever 224 moves from a position substantially outside the handle 220 (open) to a position substantially within the handle 220 (closed).

Figure 2F:
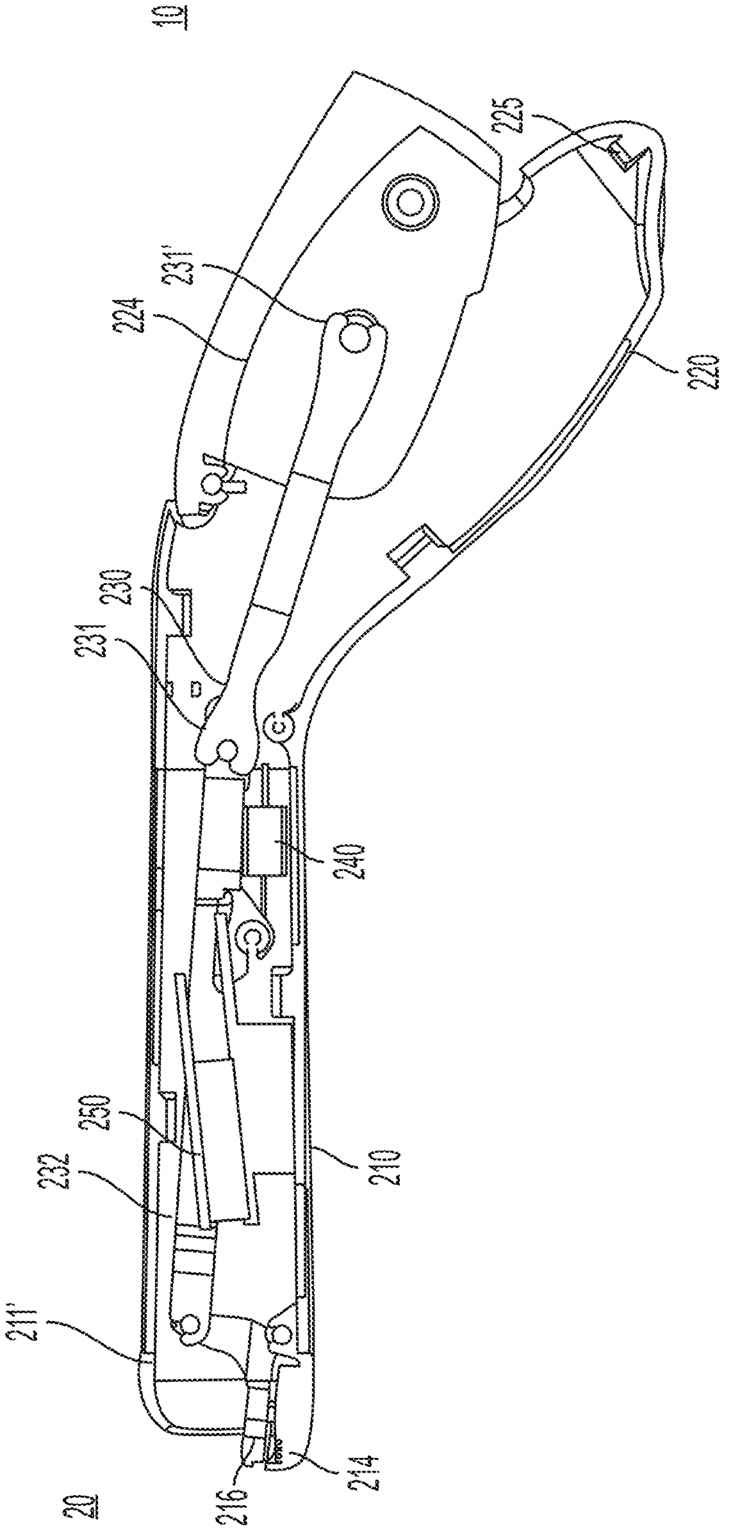

The horizontal link 232 is elongated and has a first horizontal link mating surface 233 configured to engage the second grasper element 216 and a second horizontal link mating surface 233' configured to engage the first actuating link mating surface 231 of the actuating link 230. In one configuration, the first horizontal link mating surface 233 and the second horizontal link mating surface 233' are not positioned within the same plane as is appreciated by reviewing FIGS. 2C and 2F. When the lever is in a closed position, as shown in FIGS. 2C and 2F, the distal end 20 of the actuating link 230 is angled towards a lower interior surface 211 within the housing 210, and the distal end 20 of the horizontal link 232 is angled towards an upper interior surface 211' within the housing 210 which puts a downward pressure of the second grasper element 216 thereby placing the second grasper element 216 in a closed position. When the lever is in an open position, as shown in FIGS. 2D and 2E, the distal end 20 of the actuating link 230 moves away from the lower interior surface 211 within the housing 210, and the distal end 20 of the horizontal link 232 moves away from the upper interior surface 211' within the housing 210 towards the middle of the interior of the housing 210 which removes the downward pressure of the second grasper element 216 thereby placing the second grasper element 216 in an open position so that the facing surface of the second grasper element does not engage the facing surface of the first grasper element.

Figure 2G:
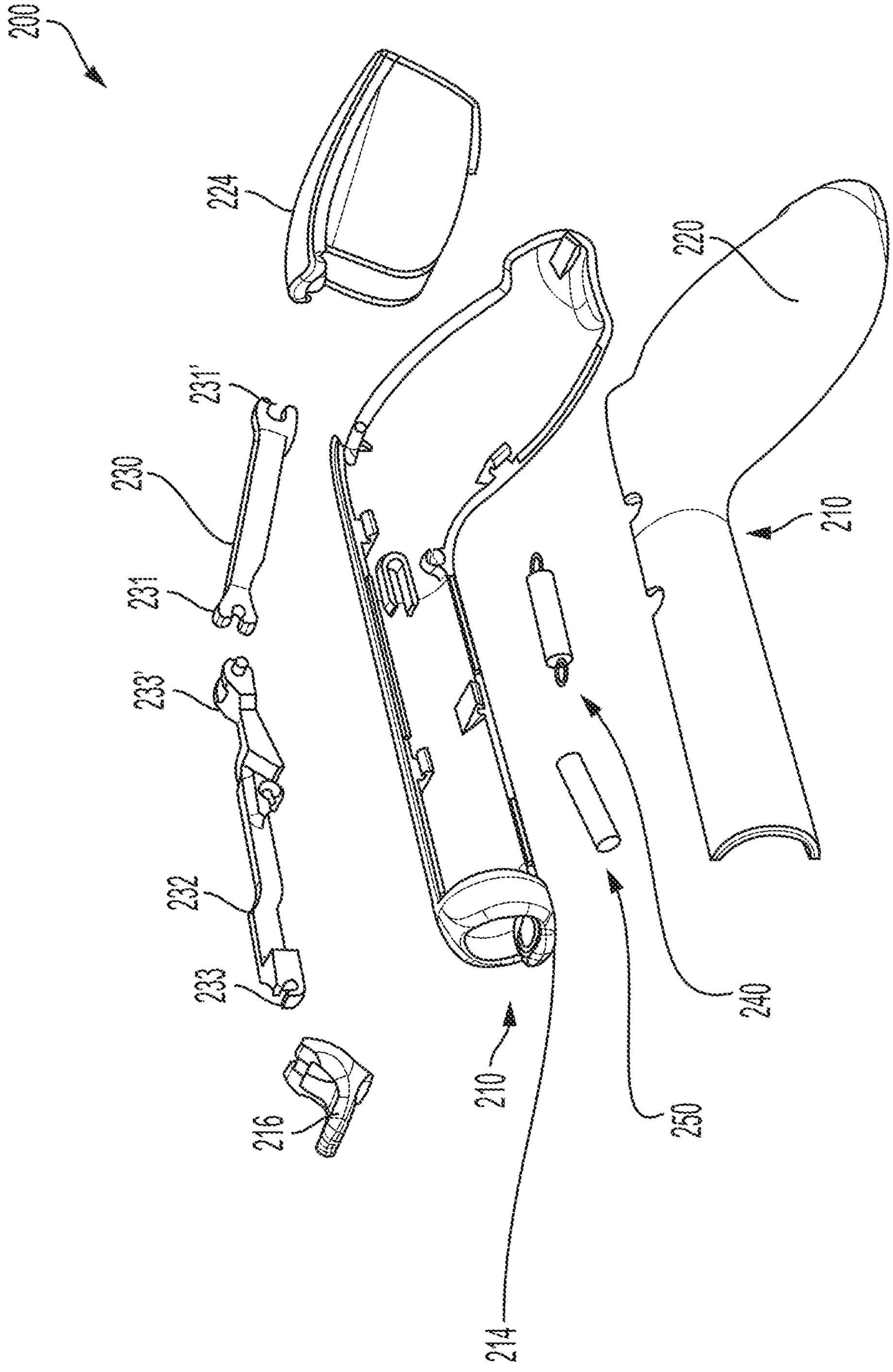

An exploded view of the parts of the IUD removal device 200 is shown in FIG. 2G. Also provided is a spring 240 and a camera 250. A cable can also be provided that connects the camera 250 to, for example, a power sources or a mobile device. The camera allows images obtained via the distal end of the IUD removal device to be provided to an electronic device, such as an electronic device with a screen. The camera and/or IUD removal device can be connected via a wire or wirelessly to the electronic device with a screen. Alternatively, the camera can be wirelessly connectable to the IUD removal device.

The spring 240 is operable to keep the lever 224 in the outer position extended away from the body of the handle as a default location. The spring 240 is attached to the horizontal link 232 on the front end of the spring and to the handle 220 on the back end of the spring 240, e.g. left side of housing.

Figure 3B:
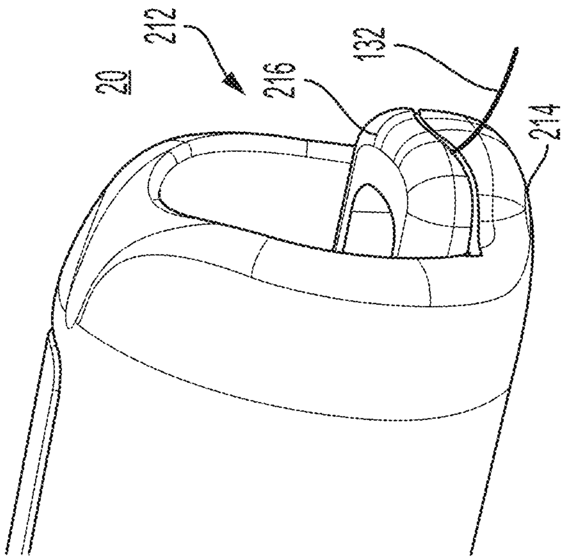
FIGS. 3A-B illustrate a close-up of the distal end of the IUD grasper with the IUD thread on bottom of the grasper (FIG. 3A), and the IUD secured between the first and second grasper elements (FIG. 3B)
Figure 3A:
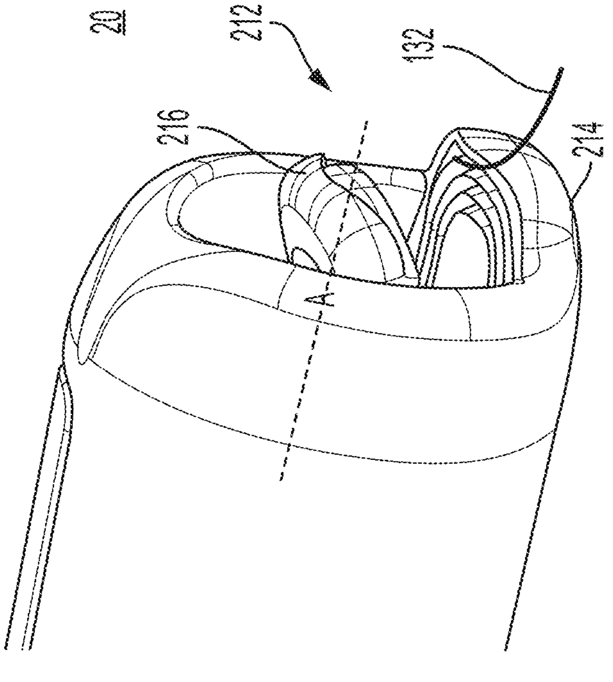
Figure 4:
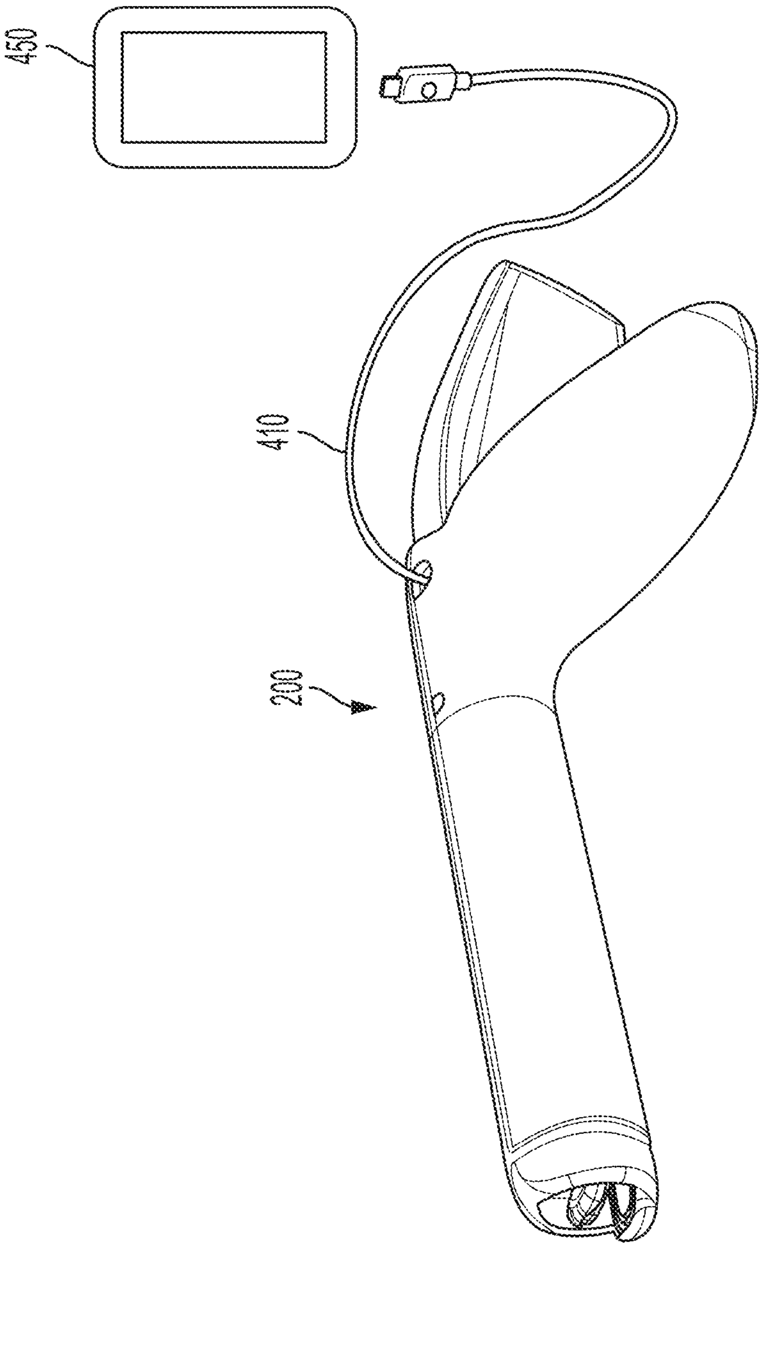
FIG. 4 illustrates an IUD removal device with a cable for connecting to a mobile device.

FIGS. 3A-B illustrate a close-up of the distal end 20 of the IUD removal device 200 with the IUD thread 132 on bottom of the grasper (FIG. 3A), and the IUD thread 132 secured between the second grasper element 216 and the first grasper element 214 (FIG. 3B) when the lever (shown in FIG. 2) is moved to the closed position. The leading edge of the lower (or fixed) grasper element is raised. The raised leading edge 215 facilitates getting the threads of the IUD into the grasper. Teeth can also be provided on the interior surface of one or both of the grasper elements such that the teeth on the interior surface faces the face of the opposing grasper element.

III. Method of Removing an IUD

Figure 5A:
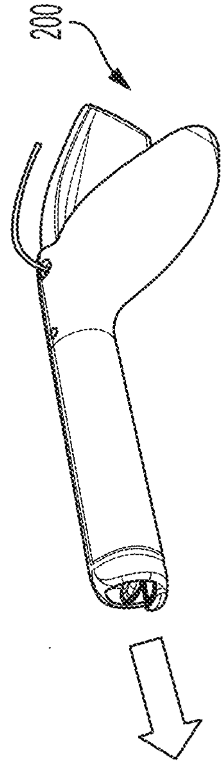
FIGS. 5A-D illustrate the device at different points during use.
Figure 5B:
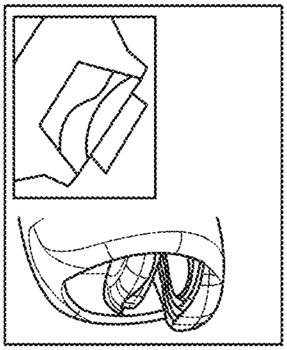
Figure 5C:
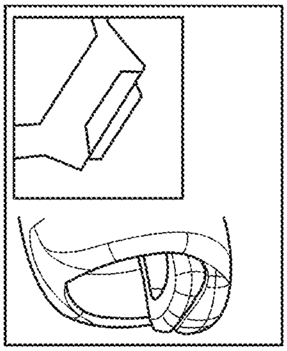

In use, once any packaging is removed, the IUD removal device 200 is advanced into the vaginal canal with the graspers in an open configuration as shown in FIGS. 5A-B. A camera can be used allow the user or a third person to visualize on a screen the location of the threads relative to the distal opening of the IUD removal device and the graspers. The third person can be remotely located from the user. The camera can communicate an image, images, or video to an external device with a screen via wire or wirelessly. Instructional videos and content can also be viewed on the screen. FIG. 5B is a close-up showing the upper grasper 216 and lower grasper 214 (e.g., jaw) in an open configuration and FIG. 5C is a close-up showing the upper grasper 216 and lower grasper 214 in a closed configuration.

Figure 5D:
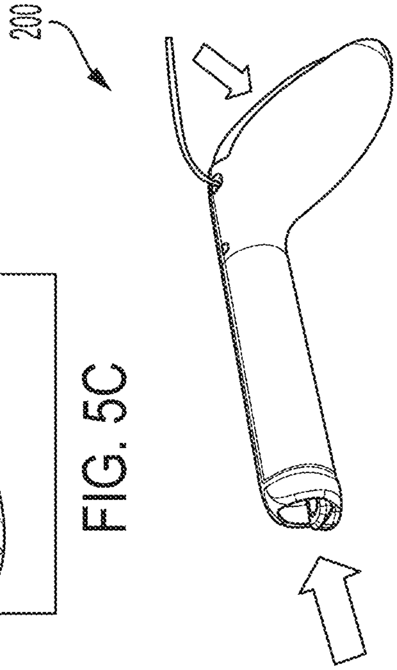

The IUD removal device and/or camera can be provided with or without additional functions such as a light element to facilitate viewing. Suitable light element is an LED light. Once the IUD threads are positioned between the grasper elements, the lever is moved towards the body of the housing which moves the graspers into a closed configuration as shown in FIGS. 5C-D. The camera can be engaged via a camera cable or via a wireless connection such as Bluetooth. The cable engages the IUD removal device via a cable connection aperture on the housing of the IUD removal device. The IUD removal device 200 is then pulled proximally which should cause the IUD to be withdrawn. The graspers may have a locking element to keep the graspers closed. Alternatively, the user can continue to squeeze the handle during removal. Locking elements include, but are not limited to, ratchets, cams, friction features, gears, and latches.

IV. Kits

An IUD removal device kit can also be provided. In addition to a removal device, the kit includes a reflective surface, and a cable 410 for connecting the IUD removal device to an external device such as a mobile device 450, such as a phone. The cable can include a USB connector. The reflective surface can be particularly useful for configurations of removal devices that do not include a camera.

A self-illuminating cone assembly can also be provided. Additional components of the kit can include forceps and a forceps guide. The self-illuminating cone assembly can be similar to a self-contained amnioscope which provides a shadow-free light source and allows access to the vagina 34. The forceps have a 90 degree bend and pass through a forceps guide in the self-illuminating cone assembly to access the cervix 32. The forceps can be used to grab the IUD threads in order to position the IUD threads optimally for the IUD removal device to securely engage the threads. The reflective surface, such as a mirror or phone mount attached to the self-illuminating cone assembly, provides visual feedback during the removal procedure. A vaginal canal measurement device can be provided to assist in determining the depth of the vaginal canal. A software application ("app") can also be provided for an electronic device that allows a patient (or partner) to upload a picture of the removed IUD to provide digital confirmation of successful removal.

V. Software

As part of the IUD removal device system, a software application can be provided and downloaded to a memory on an electronic device or stored on a memory associated with the IUD removal device. The software can be operable to provide audible instructions and/or visual instructions (static (e.g. pictures), non-static (e.g. video), or a combination thereof). The memory, which may be internal memory or external memory to a microcontroller, may be implemented in firmware and/or software implementation. The firmware and/or software implementation methodologies may be implemented with modules (e.g., procedures, functions, and so on) that perform the functions described herein. A machine-readable medium tangibly embodying instructions may be used in implementing the methodologies described herein. For example, software codes may be stored in a memory and executed by a processor unit (e.g., microcontroller). Memory may be implemented within the processor unit or external to the processor unit. As used herein, the term "memory" refers to types of long term, short term, volatile, nonvolatile, and/or other non-transitory memory and is not to be limited to a particular type of memory or number of memories, or type of media upon which memory is stored.

If implemented in firmware and/or software, and/or as part of microcontroller and/or memory, the functions described herein may be stored as one or more instructions or code on a computer-readable medium. Examples include computer-readable media encoded with a data structure and computer-readable media encoded with a computer program. Computer-readable media includes physical computer storage media. A storage medium may be an available medium that can be accessed by a computer. By way of example, and not limitation, such computer-readable media can include RAM, ROM, EEPROM, CD-ROM or other optical disk storage, magnetic disk storage or other magnetic storage devices, or other medium that can be used to store desired program code in the form of instructions or data structures and that can be accessed by a computer (e.g., microcontroller); disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

In addition to storage on computer readable medium, instructions and/or data may be provided as signals on transmission media included in a communication apparatus. For example, a communication apparatus may include a transceiver having signals indicative of instructions and data. The instructions and data are configured to cause one or more processors (e.g., microcontroller) to implement the functions outlined.

While preferred embodiments of the present invention have been shown and described herein, it will be obvious to those skilled in the art that such embodiments are provided by way of example only. Numerous variations, changes, and substitutions will now occur to those skilled in the art without departing from the scope of the invention. For example, the use of comprise, or variants such as comprises or comprising, includes a stated integer or group of integers but not the exclusion of any other integer or group of integers. It should be understood that various alternatives to the embodiments of the invention described herein may be employed in practicing the invention. It is intended that any claims presented at any time in this application define the scope of the invention and that methods and structures within the scope of these claims and their equivalents are covered thereby.

What is claimed:

1. An IUD removal device comprising:
- a housing defining a cavity having a handle at a proximal end and an aperture at a distal end;
- a grasper positioned within the cavity wherein the grasper extends outside the aperture at the distal end, the grasper comprising
- a first stationary grasper element with a first facing surface, and
- a second moveable grasper element with a second facing surface,
- wherein the first facing surface is positioned to face the second facing surface;
- a lever positioned adjacent the handle wherein the lever is operable to control the grasper when the lever is moved from a first position to a second position; and
- an actuating link in communication with the lever at a first end and the second moveable grasper element at a second end.

2. The IUD removal device of claim 1 further comprising one or more of a plurality of one or more of links, locking elements, and springs.

3. The IUD removal device of claim 2 wherein a locking element is operable to secure the lever in the second position.

4. The IUD removal device of claim 2 wherein the links further comprise an actuating link and a horizontal link.

5. The IUD removal device of claim 1 wherein the IUD removal device is in communication with one or more of a camera and a light.

6. The IUD removal device of claim 5 wherein the IUD removal device has a cable connection aperture for receiving a first end of a cable wherein a second end of the cable is operable to engage an electronic device.

7. The IUD removal device of claim 5 wherein the IUD removal device is in wireless communication with the camera.

8. The IUD removal device of claim 1 wherein the first stationary grasper element has a raised leading edge.

9. The IUD removal device of claim 1 wherein at least one of the first stationary grasper element and the second moveable grasper element is operable to extend beyond the aperture of the housing.

10. The IUD removal device of claim 1 wherein at least one of the first stationary grasper element and the second moveable grasper element has a gripping surface on an interiorly facing surface.

11. An IUD removal device system comprising:
- an IUD removal device comprising
  - a housing defining a cavity having a handle at a proximal end and an aperture at a distal end,
  - a grasper positioned within the cavity wherein the grasper extends outside the aperture at the distal end, the grasper comprising
  - a first stationary grasper element with a first facing surface, and
  - a second moveable grasper element with a second facing surface,
  - wherein the first facing surface is positioned to face the second facing surface;
  - a lever positioned adjacent the handle wherein the lever is operable to control the grasper when the lever is moved from a first position to a second position;
  - an actuating link in communication with the lever at a first end and the second moveable grasper element at a second end; and
- a software application downloadable to the an electronic device wherein the software application is operable to provide instructions to a user during use of the IUD removal device.

12. The IUD removal device system of claim 11 further comprising one or more of a plurality of one or more of links, locking elements, and springs.

13. The IUD removal device system of claim 12 wherein the locking element is operable to secure the lever in the second position.

14. The IUD removal device system of claim 12 wherein the links further comprise an actuating link and a horizontal link.

15. The IUD removal device system of claim 11 wherein the IUD removal device is in communication with one or more of a camera and a light.

16. The IUD removal device system of claim 15 wherein the IUD removal device has a cable connection aperture for receiving a first end of a cable wherein a second end of the cable is operable to engage an electronic device.

17. The IUD removal device system of claim 16 wherein the IUD removal device is in wireless communication with the camera and the software application.

18. The IUD removal device system of claim 11 wherein the first stationary grasper element has a raised leading edge.

19. The IUD removal device system of claim 11 wherein at least one of the first stationary grasper element and the second moveable grasper element is operable to extend beyond the aperture of the housing.

20. The IUD removal device system of claim 11 wherein at least one of the first stationary grasper element and the second moveable grasper element has a gripping surface on an interiorly facing surface.

21. An IUD removal device kit comprising:

an IUD removal device comprising a housing defining a cavity having a handle at a proximal end and an aperture at a distal end, a grasper positioned within the cavity wherein the grasper extends outside the aperture at the distal end, the grasper comprising a first stationary grasper element with a first facing surface, and a second moveable grasper element with a second facing surface, wherein the first facing surface is positioned to face the second facing surface, a lever positioned adjacent the handle wherein the lever is operable to control the grasper when the lever is moved from a first position to a second position, and an actuating link in communication with the lever at a first end and the second moveable grasper element at a second end;

one or more of a cable with a USB connector, a reflective surface, a self- illuminating cone assembly, forceps, forceps guide, vaginal canal measurement device.

22. The IUD removal device kit of claim 21 further comprising a software application.

23. A method of using an IUD removal device comprising:

providing the IUD removal device wherein the IUD removal device comprises a housing defining a cavity having a handle at a proximal end and an aperture at a distal end, a grasper positioned within the cavity wherein the grasper extends outside the aperture at the distal end, the grasper comprising a first stationary grasper element with a first facing surface, and a second moveable grasper element with a second facing surface, wherein the first facing surface is positioned to face the second facing surface, a lever positioned adjacent the handle wherein the lever is operable to control the grasper when the lever is moved from a first position to a second position, and an actuating link in communication with the lever at a first end and the second moveable grasper element at a second end;

inserting the IUD removal device into a vaginal canal with the grasper in an open configuration;

visualizing a location of one or more IUD threads with a camera;

positioning the IUD threads between the first stationary grasper element and the second moveable grasper element;

activating the grasper to change the grasper from the open configuration to a closed configuration; and withdrawing the IUD removal device from the vaginal canal.

24. A method of using an IUD removal device comprising:

providing the IUD removal device wherein the IUD removal device comprises a housing defining a cavity having a handle at a proximal end and an aperture at a distal end, a grasper positioned within the cavity wherein the grasper extends outside the aperture at the distal end, the grasper comprising a first stationary grasper element with a first facing surface, and a second moveable grasper element with a second facing surface, wherein the first facing surface is positioned to face the second facing surface;

a lever positioned adjacent the handle wherein the lever is operable to control the grasper when the lever is moved from a first position to a second position, an actuating link in communication with the lever at a first end and the second moveable grasper element at a second end, and a software application downloadable to the an electronic device wherein the software application is operable to provide instructions to a user during use of the IUD removal device, and an actuating link in communication with the lever at a first end and the second moveable grasper element at a second end;

activating the software application;

inserting the IUD removal device into a vaginal canal with the grasper in an open configuration;

visualizing a location of one or more IUD threads with a camera;

following the instructions delivered via the software application;

positioning the IUD threads between the stationary first grasper element and the second moveable grasper element;

activating the grasper to change the grasper from the open configuration to a closed configuration; and withdrawing the IUD removal device from the vaginal canal.

* * * * *